(12) United States Patent
Lee et al.

(10) Patent No.: US 10,098,602 B2
(45) Date of Patent: Oct. 16, 2018

(54) APPARATUS AND METHOD FOR PROCESSING A MEDICAL IMAGE OF A BODY LUMEN

(71) Applicant: SAMSUNG ELECTRONICS CO., LTD., Suwon-si (KR)

(72) Inventors: Duhgoon Lee, Suwon-si (KR); Toshihiro Rifu, Suwon-si (KR)

(73) Assignee: SAMSUNG ELECTRONICS CO., LTD., Suwon-si (KR)

(*) Notice: Subject to any disclaimer, the term of this patent is extended or adjusted under 35 U.S.C. 154(b) by 362 days.

(21) Appl. No.: 14/550,164

(22) Filed: Nov. 21, 2014

(65) Prior Publication Data
US 2015/0141814 A1     May 21, 2015

(30) Foreign Application Priority Data

Nov. 21, 2013  (KR) .................. 10-2013-0142332

(51) Int. Cl.
*A61B 6/00* (2006.01)
*A61B 6/03* (2006.01)
(Continued)

(52) U.S. Cl.
CPC ............. *A61B 6/5217* (2013.01); *A61B 6/03* (2013.01); *A61B 6/037* (2013.01); *A61B 6/504* (2013.01);
(Continued)

(58) Field of Classification Search
CPC ........... A61B 6/03; A61B 6/037; A61B 6/504; A61B 6/5217; G06T 2207/10081;
(Continued)

(56) References Cited

U.S. PATENT DOCUMENTS

| 4,692,864 A | 9/1987 | Shimoni et al. |
| 5,757,877 A | 5/1998 | Wilting |

(Continued)

FOREIGN PATENT DOCUMENTS

| CN | 101882950 A | 11/2010 |
| CN | 102124471 A | 7/2011 |

(Continued)

OTHER PUBLICATIONS

Communication dated Sep. 14, 2015, issued by the Korean Intellectual Property Office in counterpart Korean application No. 10-2013-0142332.

(Continued)

*Primary Examiner* — Michael Rozanski
(74) *Attorney, Agent, or Firm* — Sughrue Mion, PLLC

(57) ABSTRACT

An apparatus includes an image analysis unit arranged to extract, from the medical image, brightness intensities of a first body lumen region of the medical image and brightness intensities of a second body lumen region of the medical image; and a measuring unit arranged to calculate a first body lumen value and a second body lumen value, each of the first body lumen value and a second body lumen value being calculated as a predetermined linear combination of the brightness intensities of the corresponding first body lumen region and second body lumen region, and to compare the first body lumen value with the second body lumen value.

15 Claims, 12 Drawing Sheets

(51) Int. Cl.
*G06T 7/00* (2017.01)
*G06T 7/62* (2017.01)

(52) U.S. Cl.
CPC .............. *G06T 7/0012* (2013.01); *G06T 7/62* (2017.01); *G06T 2207/10081* (2013.01); *G06T 2207/30101* (2013.01); *G06T 2207/30172* (2013.01)

(58) Field of Classification Search
CPC . G06T 2207/30101; G06T 2207/30172; G06T 7/0012; G06T 7/602
See application file for complete search history.

(56) References Cited

U.S. PATENT DOCUMENTS

| | | | |
|---|---|---|---|
| 5,872,861 | A | 2/1999 | Makram-Ebeid |
| 7,333,648 | B2 | 2/2008 | Edic et al. |
| 8,494,244 | B2 | 7/2013 | Dutta et al. |
| 2004/0249270 | A1 | 12/2004 | Kondo et al. |
| 2007/0116342 | A1 | 5/2007 | Zarkh et al. |
| 2008/0025587 | A1 | 1/2008 | Asbeck |
| 2008/0317310 | A1 | 12/2008 | Suresh et al. |
| 2009/0169076 | A1 | 7/2009 | Lobregt et al. |
| 2009/0304252 | A1 | 12/2009 | Hyun et al. |
| 2010/0040263 | A1 | 2/2010 | Li et al. |
| 2010/0076296 | A1 | 3/2010 | Mittal et al. |
| 2011/0071404 | A1 | 3/2011 | Schmitt et al. |
| 2012/0051606 | A1 | 3/2012 | Saikia |
| 2012/0226141 | A1 | 9/2012 | Shinoda et al. |

FOREIGN PATENT DOCUMENTS

| | | |
|---|---|---|
| KR | 1020090127101 A | 12/2009 |
| KR | 1020130079694 A | 7/2013 |

OTHER PUBLICATIONS

Communication dated Mar. 12, 2015 issued by the Int. Searching Authority in counterpart Application No. PCT/KR2014/011242 (PCT/ISA/210 & 237).

Communication dated Mar. 30, 2015 issued by the European Patent Office in counterpart Application No. 14194256.5.

Communication dated May 4, 2018 issued by the State Intellectual Property Office of P.R. China in counterpart Chinese Patent Application No. 201480073766.0.

Communication dated Apr. 6, 2018 issued by the European Patent Office in counterpart European Patent Application No. 14194256.5.

$$S_d = \left(1 - \frac{dm}{dr}\right) \times 100\%$$

Vc

APPARATUS AND METHOD FOR PROCESSING A MEDICAL IMAGE OF A BODY LUMEN

CROSS-REFERENCE TO RELATED APPLICATION

This application claims priority from Korean Patent Application No. 10-2013-0142332, filed on Nov. 21, 2013 in the Korean Intellectual Property Office, the disclosure of which is incorporated herein by reference in its entirety.

BACKGROUND

1. Field

One or more embodiments of the present invention relate in general to an apparatus and method for processing a medical image, and more particularly, to an apparatus and method for processing a medical image in order to quantify the size of a body lumen, such as a blood vessel or urinary tract. More in particular, the invention relates to an apparatus and method for processing a medical image in order to accurately measure the degree of stenosis in a body lumen, such as a blood vessel or urinary tract.

2. Description of the Related Art

An apparatus for processing a medical image acquires an image of an internal structure of an object through non-invasive inspection, thereby allowing a medical practitioner to observe inner parts of a human body by imaging and processing details of internal structures, organs, and flow of fluids. Medical images output by the apparatus are then used to diagnose the medical condition and disease of a patient. The apparatus may be a magnetic resonance imaging (MRI) apparatus, a computed tomography (CT) apparatus, an X-ray apparatus, or an ultrasound apparatus, and is configured to process scanned image data and create medical images. Medical images may include 2D images, e.g. projections or slices, and 3D images.

A CT apparatus may provide a cross-section image of an object to thereby allow a user to observe a non-overlapping representation of an internal structure (e.g., organs such as the kidneys and the lungs), compared to a general X-ray apparatus.

However, since a CT image has a resolution of about 0.7 mm, it is difficult to image blood vessels having a diameter of several millimeters (mm). Furthermore, some blood vessels such as coronary arteries may move due to the heart beats during a CT scan. Such a movement may cause various artifacts such as motion artifacts in a reconstructed CT image.

To diagnose blood vessel diseases such as coronary artery stenosis and cardiovascular diseases, it is necessary to accurately interpret a medical image and detect abnormal blood vessels. However, as described above, due to the small diameter of the blood vessels and movements thereof during imaging, it is difficult to accurately interpret a CT image and diagnose a blood vessel disease.

Thus, there is a need for a method and apparatus for processing a medical image in order to correctly analyze a CT image and accurately diagnose a blood vessel disease such as stenosis.

SUMMARY

One or more embodiments of the present invention include an apparatus and method for processing a medical image in order to accurately diagnose of the degree of stenosis of body lumens, such as blood vessels, and/or detect stenosis regions in body lumens, and more particularly, an apparatus and method for processing a medical image in order to accurately diagnose the degree of stenosis of coronary arteries in a computed tomography (CT) image.

Additional aspects will be set forth in part in the description which follows and, in part, will be apparent from the description, or may be learned by practice of the presented embodiments.

According to one or more embodiments of the present invention, an apparatus for processing a medical image of a body lumen includes an image analysis unit arranged to extract from the medical image brightness intensities of a first body lumen region of the medical image and brightness intensities of a second body lumen region of the medical image, and a measuring unit arranged to calculate a first body lumen value and a second body lumen value, each value being calculated as a predetermined linear combination of the brightness intensities of the corresponding region, and further arranged to compare the first body lumen value with the second body lumen value.

The body lumen is for example a blood vessel or a urinary tract.

The brightness intensities may correspond to intensity values of image signals in each of the first body lumen region and the second body lumen region.

The brightness intensities may correspond to pixel values or voxel values of the medical image.

The number of intensity values extracted may be the same for the first body lumen region and the second body lumen region. The size of the first body lumen region is the same as the size of the second body lumen region. The shape of the first body lumen region is the same as the shape of the second body lumen region.

The image analysis unit may extract a center line of the body lumen from the medical image.

The first body lumen region may be substantially perpendicular to the center line of the body lumen at a first position along the center line and the second body lumen region may be perpendicular to the center line at a second position along the center line, different from the first position.

The medical image may be a 3D medical image or a 2D medical image.

When the medical image is a 3D medical image, the image analysis unit may be arranged to extract from the 3D medical image a first cross section image of the body lumen in a plane perpendicular to the center line at the first position and a second cross section image of the body lumen in a plane perpendicular to the center line at the second position, and further arranged to extract the brightness intensities of the first body lumen region from said first cross section image and extract the brightness intensities of the second body lumen region from said second cross section image.

The first cross section image is associated with the first body lumen region and the second cross section image is associated with the second body lumen region. A linear combination of the intensities (e.g. pixel values) of these cross section images gives a measure correlated to the area of the body lumen at the respective regions, and thus to the size of the body lumen in the respective regions.

In another embodiment, the medical image is a 3D medical image and the image analysis unit is arranged to extract from the 3D medical image a projection image by projecting the medical image on a plane having a normal substantially perpendicular to the center line of the body lumen and the image analysis unit is arranged to extract the brightness intensities of the first and second body lumen regions from the projection image.

In another embodiment, the medical image is a 2D medical image corresponding to such a projection image, i.e. a projection of the body lumen in a plane having a normal substantially perpendicular to the center line of the body lumen, wherein the image analysis unit is arranged to extract the brightness intensities of the first and second body lumen regions from the projection image.

The projection image is a 2D image, from which a 2D rectangle or 1D line may be extracted which is substantially perpendicular to the center line, as first body lumen region and/or second body lumen region.

The center line of the body lumen will normally not have the same direction over its entire length. It is understood that the projection plane described above has a normal, i.e. a line perpendicular to the plane surface, perpendicular to the center line at a given point along the center line, not necessarily perpendicular to all points of the center line. For example, the projection plane is orientated such that its normal is perpendicular to an average direction of the center line or perpendicular to the center line at a particular point along the center line.

The first and second body lumen regions are perpendicular to the center line. For example, the first and/or second body lumen region may be a line substantially perpendicular to the center line, or include a series of perpendicular lines along the center line. In another example, the intensities are extracted from a rectangular region perpendicular to the center line. The region for extracting the intensities (e.g. pixel values of voxel values) may have a predetermined size, such that the size of the region is the same for the first region and the second region.

For example, the predetermined size is based on experimental data, and optimized for each vessel. In another example, a vessel diameter is obtained using related art techniques and a fixed margin (percentage or absolute) is added to define the size of the regions. For example, the maximum vessel diameter of the medical image is used to define the predetermined size of the regions, wherein optionally a margin is applied. In another example, the average vessel diameter of the medical image is used to define the predetermined size of the regions, wherein optionally a margin is applied. The predetermined size of the regions may be adjustable, e.g. by user input.

The predetermined linear combination may be a weighted sum, wherein the weighting factor is the same for the first region and the second region. The linear combination is a sum, i.e., the intensities are weighted with a factor one.

The first body lumen region may correspond to a normal body lumen region and the second body lumen region may correspond to a stenosis body lumen region. In this case, the measuring unit may generate a measure of the degree of stenosis of the body lumen in the stenosis body lumen region on the basis of the comparison between the first body lumen value and the second body lumen value.

The measuring unit may be arranged to generate the measure of the degree of stenosis by using a ratio between the first body lumen value and the second body lumen value. The measuring unit may generate the measure of the degree of stenosis by using a difference between the first body lumen value and the second body lumen value.

The image analysis unit may be arranged to segment the medical image, e.g. segmenting an area of the body lumen in the medical image.

The medical image may be a computed tomography (CT) image.

The medical image may include a CT image obtained by multi-energy CT capturing after injection of contrast media.

The medical image may include a CT image obtained by multi-energy CT capturing after injection of contrast media. For example, the medical image includes an iodine map.

The apparatus may further include an input unit configured to receive the normal and stenosis body lumen regions from a user.

The apparatus may further include an output unit to display the medical image. For example, the output unit is configured to display a projection image or cross section image of the body lumen on the basis of the medical image. For example, the user may select a normal region and a stenosis region by selecting a region displayed on the output unit.

The image analysis unit may identify a diameter of the body lumen in the medical image and extract the normal body lumen region and the stenosis body lumen region based on a change in the diameter of the body lumen.

The measuring unit may be arranged to determine whether the second body lumen region is a stenosis body lumen region on the basis of the comparison between the first body lumen value and the second body lumen value.

In other words, the comparison between the linear combination of brightness intensities of the two body lumen regions may be used to detect a stenosis body region.

The body lumen is a blood vessel, such as a coronary artery.

The apparatus may further include an image acquisition unit for receiving the medical image.

The apparatus may further include a preprocessor for performing image pre-processing on the medical image.

The pre-processor may receive the medical image and removes at least one of a calcium area, a plaque area, and a blood vessel branch point from the medical image.

According to one or more embodiments of the present invention, a method of processing a medical image of a body lumen includes: extracting from the medical image brightness intensities of a first body lumen region and brightness intensities of a second body lumen region and calculating a first body lumen value and a second body lumen value, each value being calculated as a predetermined linear combination of the brightness intensities of the corresponding region, and comparing the first body lumen value with the second body lumen value.

The same advantages and effects apply to the method according to the invention as described above with respect to the apparatus according to the invention. In particular, the features of the apparatus and the method may be combined as desired.

The method may further include extracting a center line of the body lumen from the medical image.

The method may further include that the first body lumen region is substantially perpendicular to the center line of the body lumen at a first position along the center line and the second body lumen region is substantially perpendicular to the center line at a second position along the center line, different from the first position.

The method may further include that the medical image is a 3D medical image and the method further includes extracting from the 3D medical image a first cross section image of the body lumen in a plane substantially perpendicular to the center line at the first position, extracting a second cross section image of the body lumen in a plane substantially perpendicular to the center line at the second position and extracting the brightness intensities of the first body lumen region from the first cross section image and extracting the brightness intensities of the second body lumen region from the second cross section image.

In other words, the first body lumen region corresponds to the first cross section image and the second body lumen region corresponds to the second cross section image.

The method may further include that the medical image is a 3D medical image and the method further includes extracting from the 3D medical image a projection image by projecting the medical image on a plane having a normal substantially perpendicular to the center line of the body lumen and extracting the brightness intensities of the first and second body lumen regions from the projection image.

In other words, the first and second body lumen regions are regions of the projection image, e.g., distinct regions.

The method may include that the medical image is a 2D medical image corresponding to a projection image of the body lumen in a plane having a normal substantially perpendicular to the center line of the body lumen and the method further includes extracting the brightness intensities of the first and second body lumen regions from the projection image.

Also for this last embodiment, the first and second body lumen regions are regions of the projection image, e.g., distinct regions.

The method may further include that the predetermined linear combination is the sum of the respective brightness intensities.

The method may further include that the first body lumen region is a normal body lumen region and the second body lumen region is a stenosis body lumen region, further including generating a measure of the degree of stenosis of the body lumen in the stenosis body lumen region on the basis of the comparison between the first body lumen value and the second body lumen value.

The method may include generating the measure of the degree of stenosis by using a ratio between the first body lumen value and the second body lumen value.

The method may further include that the generating of the measure of the degree of stenosis is performed by using a difference between the first body lumen value and the second body lumen value.

The method may further include acquiring a cross-section image of the body lumen containing the center line of the body lumen.

The method may further include acquiring a CT projection image obtained by projecting the medical image on a direction perpendicular to the center line of the body lumen.

The method may further include acquiring an image obtained by segmenting the area of the body lumen in the medical image.

The medical image may be a 3D CT image.

The medical image may include a CT image obtained by multi-energy CT imaging after injection of contrast media.

The method may further include receiving the normal and stenosis regions from input provided by a user. For example, the method includes receiving parameters from the user defining the respective regions, e.g. coordinates and/or size parameters.

The method may further include displaying the medical image and receiving the normal and stenosis body lumen regions in the displayed medical image from a user.

The method may further include identifying a diameter of a body lumen in the medical image and extracting the normal body lumen region and the stenosis body lumen region based on a change in the diameter of the body lumen.

The method may further include determining whether the second body lumen region is a stenosis lumen region on the basis of the comparison between the first body lumen value and the second body lumen value.

The body lumen is a blood vessel, such as a coronary artery.

The method may further include receiving the medical image and performing image pre-processing on the medical image.

The performing of image pre-processing on the medical image may include receiving the medical image and removing at least one of a calcium area, a plaque area, and a blood vessel branch point from the medical image.

BRIEF DESCRIPTION OF THE DRAWINGS

These and/or other aspects will become apparent and more readily appreciated from the following description of the embodiments, taken in conjunction with the accompanying drawings in which.

DETAILED DESCRIPTION

Figure 1:
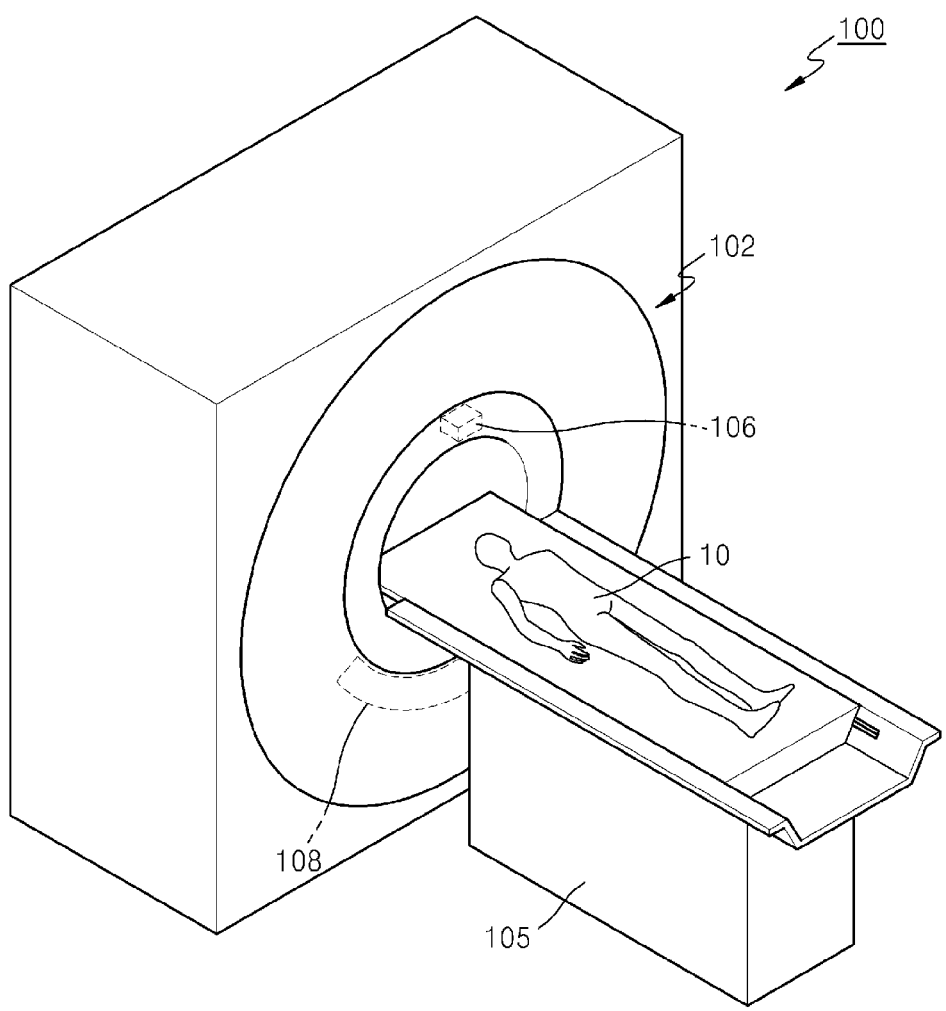
FIG. 1 is a schematic diagram of a general computed tomography (CT) system.

Advantages and features of one or more embodiments of the present invention and methods of accomplishing the same may be understood more readily by reference to the following detailed description of the embodiments and the accompanying drawings. In this regard, the present embodiments may have different forms and should not be construed as being limited to the descriptions set forth herein. Rather, these embodiments are provided so that this disclosure will be thorough and complete and will fully convey the concept of the present embodiments to one of ordinary skill in the art, and the present invention will only be defined by the appended claims. Like reference numerals refer to like elements throughout the specification.

Hereinafter, the terms used in the specification will now be briefly defined, and the embodiments will now be described in detail.

All terms including descriptive or technical terms which are used herein should be construed as having meanings that are obvious to one of ordinary skill in the art. However, the terms may have different meanings according to an intention of one of ordinary skill in the art, precedent cases, or the appearance of new technologies. Also, some terms may be arbitrarily selected by the applicant, and in this case, the meaning of the selected terms will be described in detail in the detailed description of the invention. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term 'unit' in the embodiments of the present invention means a software component or hardware components such as a field-programmable gate array (FPGA) or an application-specific integrated circuit (ASIC), and performs a specific function. However, the term 'unit' is not limited to software or hardware. The 'unit' may be formed so as to be in an addressable storage medium, or may be formed so as to operate one or more processors. Thus, for example, the term 'unit' may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and 'units' may be associated with the smaller number of components and 'units', or may be divided into additional components and 'units'.

Reference will now be made in detail to embodiments, examples of which are illustrated in the accompanying drawings. In this regard, the present embodiments may have different forms and should not be construed as being limited to the descriptions set forth herein. In the following description, well-known functions or constructions are not described in detail since they would obscure the embodiments with unnecessary detail.

Expressions such as "at least one of," when preceding a list of elements, modify the entire list of elements and do not modify the individual elements of the list.

Throughout the specification, an "image" may mean multi-dimensional data formed of discrete image elements (e.g., pixels in a two-dimensional (2D) image and voxels in a three-dimensional (3D) image). For example, the image may include a medical image of an object which is captured by a computed tomography (CT) image-capturing apparatus.

Throughout the specification, a "CT image" may mean an image generated by synthesizing a plurality of X-ray images that are obtained by imaging an object while a CT image-capturing apparatus rotates around at least one axis with respect to the object.

Throughout the specification, an "object" may include a human, an animal, or a part of a human or animal. For example, the object may include organs such as liver, heart, womb, brain, breast, abdomen, or the like, or a body lumen such as a blood vessel. Also, the object may include a phantom. The phantom means a material having a volume that is very close to a density and effective atomic number of an organism, and may include a sphere phantom having a characteristic similar to a physical body.

Throughout the specification, a "user" may be, but is not limited to, a medical expert including a doctor, a nurse, a medical laboratory technologist, a medial image expert, and a technician who repairs a medical apparatus.

Since a CT system is capable of providing a cross-section image of an object, the CT system may express an inner structure (e.g., an organ such as a kidney, a lung, etc.) of the object without an overlap therebetween, compared to a general X-ray capturing apparatus.

The CT system may obtain a plurality of pieces of image data with a thickness not more than 2 mm for several tens to several hundreds of times per second and then may process the plurality of pieces of image data, so that the CT system may provide a relatively accurate a cross-section image of the object. According to the related art, only a horizontal cross-section image of the object can be obtained, but this issue has been overcome due to various image reconstruction methods. Examples of 3D image reconstruction methods are as below.

A shade surface display (SSD) method: The SSD method is an initial 3D imaging method that displays only voxels having a predetermined Hounsfield Units (HU) value.

A maximum intensity projection (MIP)/minimum intensity projection (MinIP) method: The MIP/MinIP method is a 3D imaging method that displays only voxels having the greatest or smallest HU value from among voxels that construct an image.

A volume rendering (VR) method: The VR method is an imaging method capable of adjusting a color and transmittance of voxels that construct an image, according to interest areas.

A virtual endoscopy method: This method allows an endoscopy observation in a 3D image that is reconstructed by using the VR method or the SSD method.

A multi-planar reformation (MPR) method: The MPR method is used to reconstruct an image into a different cross-section image. A user may reconstruct an image in every desired direction.

An editing method: This method involves editing adjacent voxels so as to allow a user to easily observe an interest area in volume rendering.

A voxel of interest (VOI) method: The VOI method displays only a selected area in volume rendering.

A CT system 100 according to an embodiment of the present invention will now be described with reference to FIG. 1. The CT system 100 may include devices having various forms.

FIG. 1 schematically illustrates the CT system 100. Referring to FIG. 1, the CT system 100 may include a gantry 102, a table 105, an X-ray generating unit 106, and an X-ray detection unit 108.

The gantry 102 may include the X-ray generating unit 106 and the X-ray detection unit 108.

An object 10 may be positioned on the table 105.

The table 105 may move in a predetermined direction (e.g., at least one of up and down-right and left directions) during a CT imaging procedure. Also, the table 105 may tilt or rotate by a predetermined degree in a predetermined direction.

The gantry 102 may also tilt by a predetermined degree in a predetermined direction.

Figure 2:
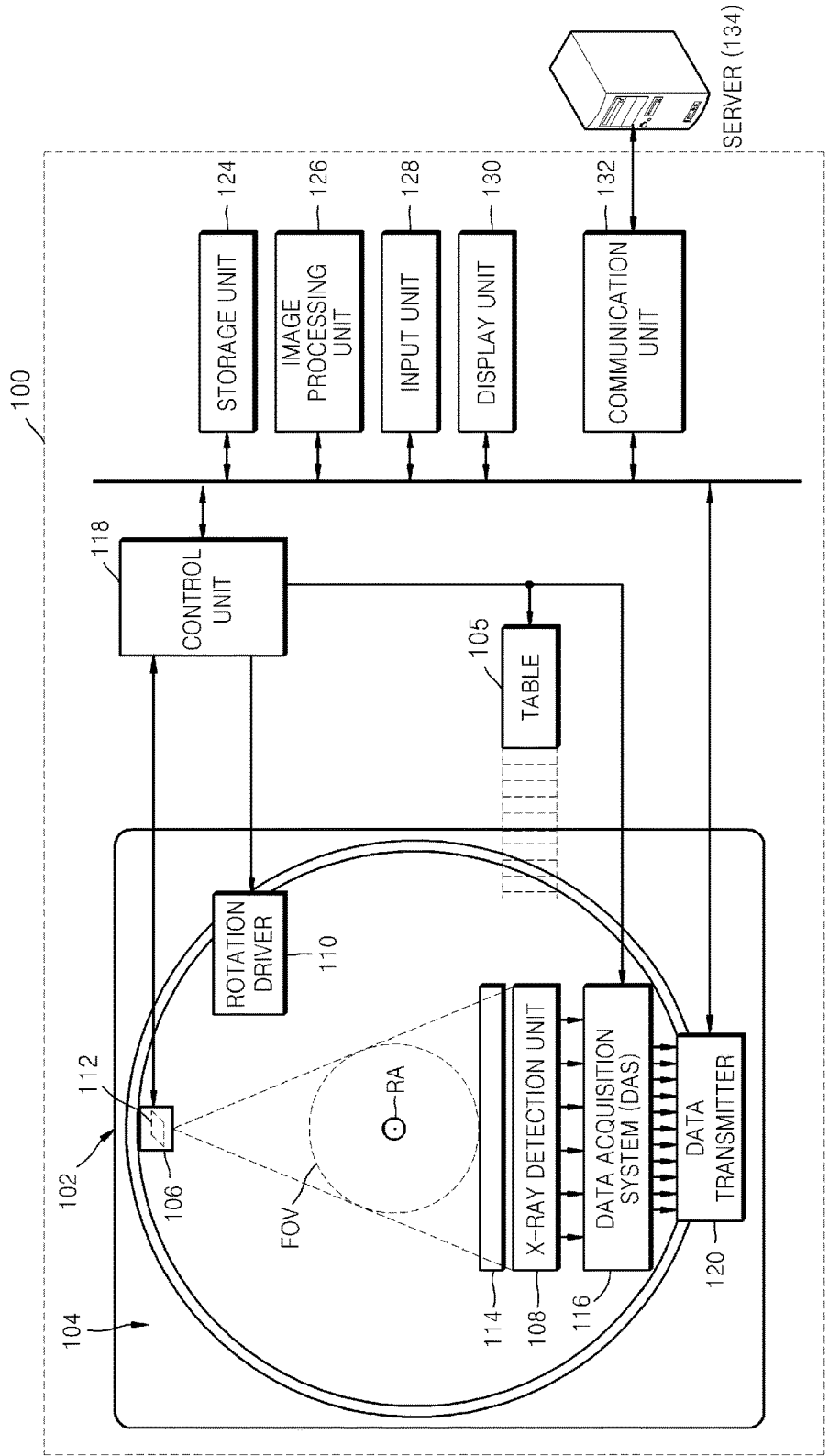
FIG. 2 illustrates a structure of a CT system according to an exemplary embodiment of the present invention.

FIG. 2 is a diagram illustrating a structure of the CT system 100.

The CT system 100 may include the gantry 102, the table 105, a control unit 118, a storage unit 124, an image processing unit 126, an input unit 128, a display unit 130, and a communication unit 132.

As described above, the object 10 may be positioned on the table 105. In the present embodiment, the table 105 may move in a predetermined direction (e.g., at least one of up and down-right and left directions), and movement of the table 105 may be controlled by the control unit 118.

The gantry 102 may include a rotating frame 104, the X-ray generating unit 106, the X-ray detection unit 108, a rotation driving unit 110, i.e., a rotation driver, a data acquisition system (DAS) 116, and a data transmitting unit 120, i.e., a data transmitter.

The gantry 102 may include the rotating frame 104 having a loop shape capable of rotating with respect to a predetermined rotation axis RA. Also, the rotating frame 104 may have a disc shape.

The rotating frame 104 may include the X-ray generating unit 106 and the X-ray detection unit 108 that face each other so as to have predetermined field of views FOV. The rotating frame 104 may also include an anti-scatter grid 114. The anti-scatter grid 114 may be positioned between the X-ray generating unit 106 and the X-ray detection unit 108.

In a medical imaging system, X-ray radiation that reaches a detector (or a photosensitive film) includes not only attenuated primary radiation that forms a valuable image but also includes scattered radiation that deteriorates a quality of an image. In order to transmit the primary radiation and to attenuate the scattered radiation, the anti-scatter grid 114 may be positioned between a patient and the detector (or the photosensitive film).

For example, the anti-scatter grid 114 may be formed by alternately stacking lead foil strips and an interspace material such as a solid polymer material, solid polymer, or a fiber composite material. However, formation of the anti-scatter grid 114 is not limited thereto.

The rotating frame 104 may receive a driving signal from the rotation driving unit 110 and may rotate the X-ray generating unit 106 and the X-ray detection unit 108 by a predetermined rotation speed. The rotating frame 104 may receive the driving signal and power from the rotation driving unit 110 while the rotating frame 104 contacts the rotation driving unit 110 via a slip ring (not shown). Also, the rotating frame 104 may receive the driving signal and power from the rotation driving unit 110 via wireless communication.

The X-ray generating unit 106 may receive a voltage and current from a power distribution unit (PDU) (not shown) via a slip ring (not shown) and then a high voltage generating unit (not shown), and then may generate and emit an X-ray. When the high voltage generating unit applies predetermined voltage (hereinafter, referred as the tube voltage) to the X-ray generating unit 106, the X-ray generating unit 106 may generate X-rays having a plurality of energy spectrums that correspond to the tube voltage.

The X-ray generated by the X-ray generating unit 106 may have a predetermined form due to a collimator 112 and then may be emitted.

The X-ray detection unit 108 may be positioned while facing the X-ray generating unit 106. The X-ray detection unit 108 may include a plurality of X-ray detecting devices. Each of the plurality of X-ray detecting devices may establish one channel but one or more embodiments of the present invention are not limited thereto.

The X-ray detection unit 108 may detect the X-ray that is generated by the X-ray generating unit 106 and that is transmitted via the object 10, and may generate an electrical signal corresponding to intensity of the detected X-ray.

The X-ray detection unit 108 may include an indirect-type X-ray detector for detecting radiation after converting the radiation into light, and a direct-type X-ray detector for detecting radiation after directly converting the radiation into electric charges. The indirect-type X-ray detector may use a scintillator. Also, the direct-type X-ray detector may use a photon counting detector. The DAS 116 may be connected to the X-ray detection unit 108. The electrical signal generated by the X-ray detection unit 108 may be wiredly or wirelessly collected by the DAS 116. Also, the electrical signal generated by the X-ray detection unit 108 may be provided to an analog-to-digital converter (not shown) via an amplifier (not shown).

According to a slice thickness or the number of slices, only some of a plurality of data collected by the X-ray detection unit 108 may be provided to the image processing unit 126 via the data transmitting unit 120, or the image processing unit 126 may select only some of the plurality of data.

The digital signal may be provided to the image processing unit 126 via the data transmitting unit 120. The digital signal may be wiredly or wirelessly provided to the image processing unit 126.

The control unit 118 may control an operation of each of modules in the CT system 100. For example, the control unit 118 may control operations of the table 105, the rotation driving unit 110, the collimator 112, the DAS 116, the storage unit 124, the image processing unit 126, the input unit 128, the display unit 130, the communication unit 132, or the like.

The image processing unit 126 may receive data (e.g., pure data before a processing operation), which is obtained from the DAS 116, via the data transmitting unit 120, and may perform pre-processing.

The pre-processing may include a process of correcting sensitivity irregularity between channels, a process of correcting a signal loss due to a rapid decrease of a signal strength or due to an X-ray absorbing material such as metal, or the like.

Data output from the image processing unit 126 may be referred as raw data or projection data. The projection data and image-capturing conditions (e.g., the tube voltage, an image-capturing angle, etc.) during obtainment of the data may be stored together in the storage unit 124.

The projection data may be a group of data values that correspond to the intensity of the X-ray that passes through the object 10. For convenience of description, it is assumed that a group of a plurality of pieces of projection data that are simultaneously obtained from all channels by a same image-capturing degree is referred as a projection data set.

The storage unit 124 may include at least one storage medium from among a flash memory-type storage medium, a hard disk-type storage medium, a multimedia card micro-type storage medium, card-type memories (e.g., an SD card, an XD memory, and the like), Random Access Memory (RAM), Static Random Access Memory (SRAM), Read-Only Memory (ROM), Electrically Erasable Programmable Read-Only Memory (EEPROM), Programmable Read-Only Memory (PROM) magnetic memory, a magnetic disc, and an optical disc.

The image processing unit 126 may reconstruct a cross-section image with respect to the object 10 by using the projection data set. The cross-section image may be a 3D image. In other words, the image processing unit 126 may reconstruct the 3D image of the object 10 by using a cone beam reconstruction method or the like, based on the projection data set.

The input unit 128 may receive an external input with respect to an X-ray tomography imaging condition, an image processing condition, or the like. For example, the X-ray tomography imaging condition may include tube voltages, energy value setting with respect to a plurality of X-rays, selection of an image-capturing protocol, selection of an image reconstruction method, setting of a FOV area, the number of slices, a slice thickness, parameter setting with respect to image post-processing, or the like. Also, the image processing condition may include resolution of an image, attenuation coefficient setting with respect to the image, setting of an image combining ratio, or the like.

The input unit 128 may include a device for receiving a predetermined input from an external source. For example, the input unit 128 may include a microphone, a keyboard, a mouse, a joystick, a touch pad, a touch pen, a voice recognition device, a gesture recognition device, or the like.

The display unit 130 may display an X-ray tomography image reconstructed by the image processing unit 126.

Exchanges of data, power, or the like between the aforementioned elements may be performed by using at least one of wired communication, wireless communication, and optical communication.

The communication unit 132 may perform communication with an external device, an external medical apparatus, etc. via a server 134 or the like. The communication will now be described with reference to FIG. 3.

Figure 3:
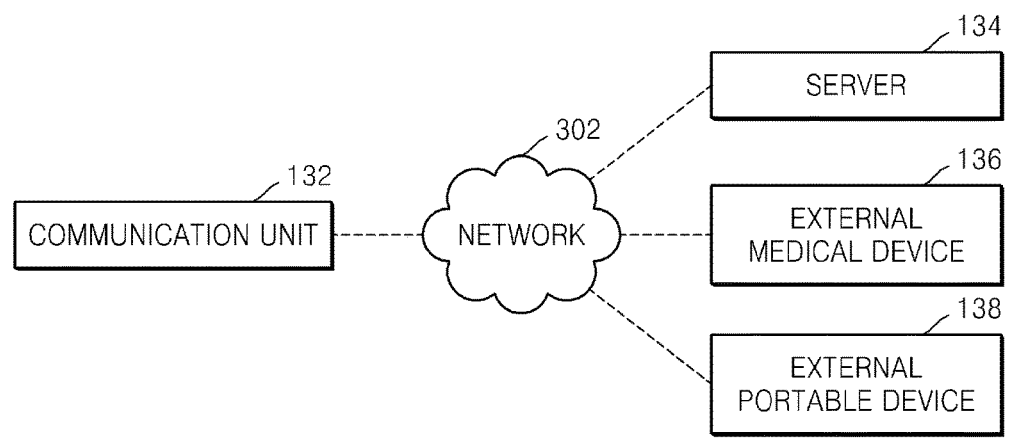
FIG. 3 illustrates a configuration of a communication unit of the CT system of FIG. 2.

FIG. 3 is a diagram illustrating a structure of the communication unit 132.

The communication unit 132 may be wiredly or wirelessly connected to a network 301 and therefore may perform communication with the server 134, an external medical apparatus 136, or an external portable device 138. The communication unit 132 may exchange data with a hospital server or other medical apparatuses in a hospital connected via a Picture Archiving and Communication System (PACS). Also, the communication unit 132 may perform data communication with the portable device 138 or the like, according to a Digital Imaging and Communications in Medicine (DICOM) standard.

The communication unit 132 may transmit and receive data related to diagnosing the object 10, via the network 301. Also, the communication unit 132 may transmit and receive a medical image obtained from the medical apparatus 136 such as a magnetic resonance imaging (MRI) apparatus, an X-ray apparatus, or the like.

Furthermore, the communication unit 132 may receive a diagnosis history or a medical treatment schedule about a patient from the server 134 and may use the diagnosis history or the medical treatment schedule in a clinical diagnosis for the patient. Also, the communication unit 132 may perform data communication with not only the server 134 or the medical apparatus 136 in a hospital but also with the portable device 138 of a user or patient.

Also, the communication unit 132 may transmit information about a device error, information about a quality control status, or the like to a system manager or a service manager via the network 301, and may receive a feedback corresponding to the information.

Figure 4:
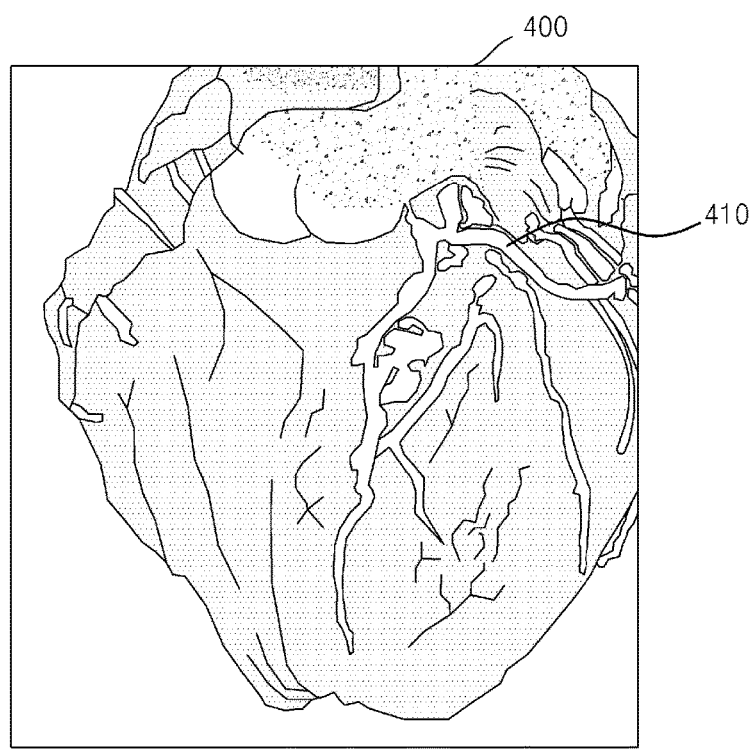
FIG. 4 illustrates a CT image of the heart.

FIG. 4 illustrates a CT image 400 of the heart.

Referring to FIG. 4, the CT image 400 is a 3D image acquired by capturing the heart, which is an object to be imaged, by using the CT system 100 of FIG. 2.

Representative examples of cardiac diseases include cardiac arrhythmia and cardiovascular diseases. Cardiovascular diseases representatively include coronary artery stenosis that may cause serious disease such as myocardial infarction, arrhythmia, and angina. Thus, the treatment of coronary artery stenosis involves an accurate diagnosis and widening or removing stenosis blood vessels.

To do so, medical images such as CT images should be analyzed to detect a stenosis blood vessel and accurately measure the degree of stenosis of the blood vessel.

A user such as a doctor may diagnose the degree of stenosis of a coronary artery 410 by referring to the CT image 400 of the heart. In detail, the user may detect a position of the coronary artery 410 where stenosis occurs in the CT image 400 and measure the degree of stenosis of the position of the coronary artery 410.

FIGS. 5A, 5B, 5C, and 5D are diagrams for explaining a method of measuring the degree of stenosis of a coronary artery by using X-ray angiography.

Figure 5A:
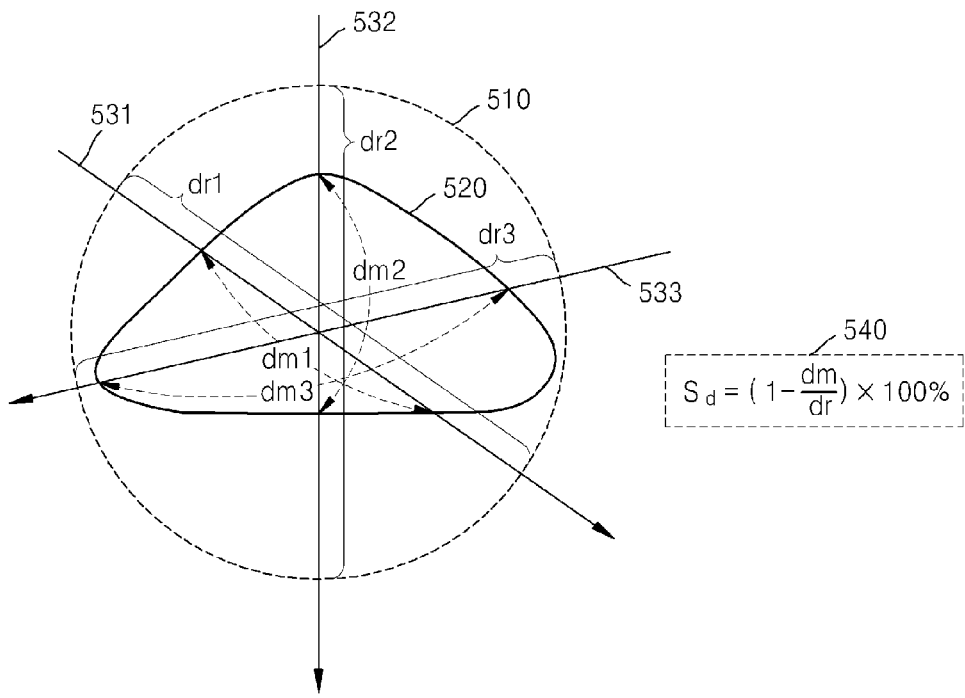
FIGS. 5A, 5B, 5C, and 5D are diagrams for explaining a method of measuring the degree of stenosis of a coronary artery.
Figure 5B:
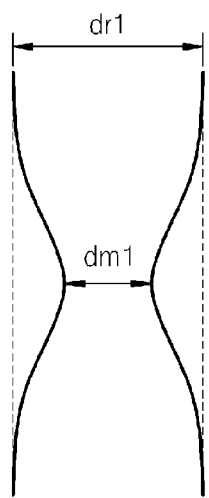
Figure 5C:
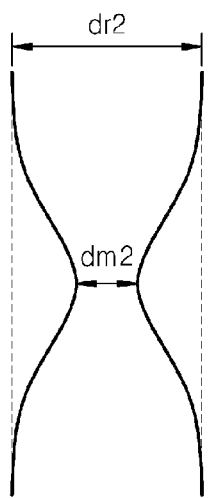
Figure 5D:
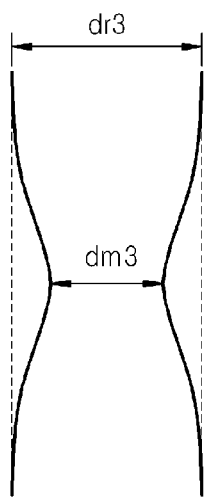

FIG. 5A illustrates a cross-section 520 of a stenosis blood vessel. FIGS. 5B through 5D illustrate longitudinal sections of the stenosis blood vessel.

Referring to FIG. 5A, the cross-section 520 of the stenosis blood vessel has a reduced size compared to a cross-section 510 of a normal blood vessel.

In general, acquiring a position of a stenosis blood vessel includes segmenting an image containing a coronary artery in a CT image, designating a position at which stenosis occurs in the segmented image, and measuring a diameter of a blood vessel as well as the degree of stenosis of the coronary artery. Segmenting the image means isolating body lumens, such as blood vessels, from other structures in the medical image or at least enhancing body lumens with respect to other structures. Reference is made to the article 'A review of 3D vessel lumen segmentation techniques: Models, features and extraction schemes', David Lesage et al., Medical Image Analysis 13 (2009) 819-845, which is hereby incorporated by reference. This article presents an overview of methods for segmenting medical images.

In the related art X-ray angiography, the degree of stenosis of a coronary artery is measured by using Equation 540, wherein dr and dm are diameters of a normal blood vessel and a stenosis blood vessel, respectively, and $S_d$ is a value indicating the degree of stenosis.

In detail, the diameter dm of the stenosis blood vessel is measured in an image of a cross-section of the stenosis blood vessel, and a value obtained by converting a ratio of the diameter dm of the stenosis blood vessel to the diameter dr of the normal blood vessel into a percentage is used as the value $S_d$ indicating the degree of stenosis of the coronary artery.

Diameters of the stenosis blood vessel and normal blood vessel may vary according to a measurement reference line. In detail, when line 531 is used as a measurement reference line, dm1 and dr1 are measured diameters of the stenosis and normal blood vessels, respectively. When line 532 is used as a measurement reference line, dm2 and dr2 are measured diameters of the stenosis and normal blood vessels, respectively. When line 533 is used as a measurement reference line, dm3 and dr3 are measured diameters of the stenosis and normal blood vessels, respectively.

FIGS. 5B through 5D illustrate the longitudinal sections of the stenosis blood vessel when the lines 531 through 533 are used as a measurement reference line, respectively.

In a method of measuring the degree of stenosis of a blood vessel by using related art X-ray angiography, the resolution of an image is not sufficiently high so as to accurately segment very thin blood vessels. Furthermore, since blood vessels move continuously during imaging, motion artifacts occur due to the movement. Thus, the accuracy of measuring the diameters of normal and stenosis blood vessels is low when related art X-ray angiography is used.

Hereinafter, apparatuses and methods for processing a medical image according to embodiments of the present invention will be described in detail with reference to FIGS. 6 through 14.

Figure 6:
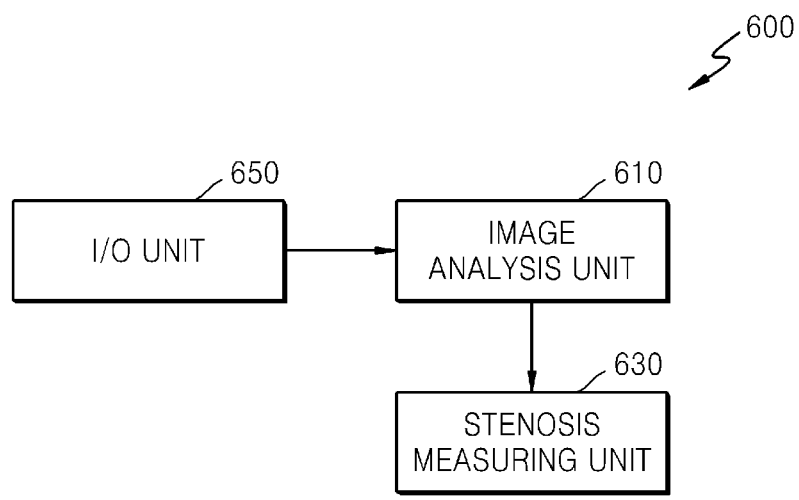
FIG. 6 is a block diagram of an apparatus for processing a medical image according to an exemplary embodiment of the present invention.

FIG. 6 is a block diagram of an apparatus 600 for processing a medical image according to an exemplary embodiment of the present invention.

Referring to FIG. 6, the apparatus 600 according to the present embodiment includes an image analysis unit 610 and a measuring unit 630. The apparatus 600 may have a configuration similar to that of the image processor 126 in FIG. 2 or the external medical device 136 in FIG. 3 that is connected to the CT system 100 in FIG. 2 via the network 301.

The apparatus 600 may further include an input and output (I/O) unit 650. The I/O unit 650 may have the same configuration as the input unit 128 and the display unit 130 described above with reference to FIG. 2.

Thus, the same descriptions as already presented with respect to FIG. 2 are omitted.

It is hereinafter assumed that a three-dimensional (3D) CT image is input as a medical image, and that the degree of stenosis of a coronary artery is measured using the 3D CT image. The medical image may alternatively be a two-dimensional (2D) CT image.

The medical image may be a CT image acquired by multi-energy CT imaging after injecting contrast media into a blood vessel.

The image analysis unit 610 acquires a first image corresponding to a portion of a blood vessel from a medical image.

In detail, the image analysis unit 610 may segment a portion of a blood vessel in the medical image. To measure the degree of stenosis of the blood vessel, the apparatus 600 according to the present embodiment is configured to segment an image containing the region of blood vessel before measuring the degree of stenosis of the blood vessel contained in the segmented image. However, segmenting the image is optional. The first image may be any image clearly showing the region of the blood vessel. In detail, the first image may be an image obtained by segmenting the region of blood vessel from the medical image. The first image may also be a longitudinal cross-section image of the blood vessel containing a center-line of the blood vessel. The first image may also be a CT projection image obtained by projecting a 3D CT image on a plane of which the normal is perpendicular to the center-line of the blood vessel.

Figure 7:
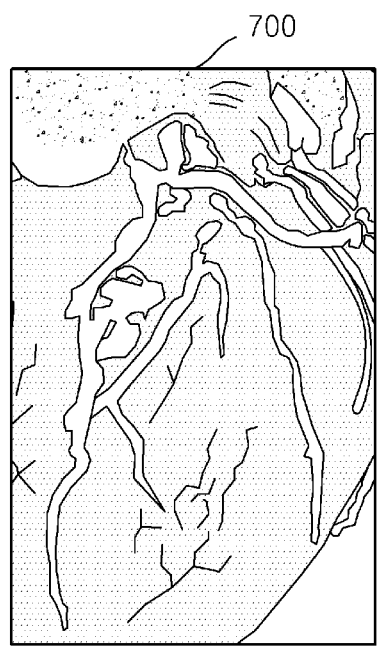
FIG. 7 is a diagram for explaining segmentation performed by an image analysis unit.

FIG. 7 is a diagram for explaining segmentation performed by the image analysis unit 610.

In detail, the image analysis unit 610 segments an image containing a portion of a blood vessel in a 3D CT image 400 obtained by X-ray irradiation. FIG. 7 illustrates a segmented image 700.

The first image may include the segmented image 700.

The measuring unit 630 acquires first information corresponding to brightness intensities of a stenosis blood vessel region and a normal blood vessel region by using the first image and produces second information indicating the degree of stenosis of the blood vessel based on the first information.

The image analysis unit 610 may also extract a center-line of a blood vessel from a portion of a blood vessel in a medical image. Reference is made to the article 'A review of 3D vessel lumen segmentation techniques: Models, features and extraction schemes', David Lesage et al., Medical Image Analysis 13 (2009) 819-845, which is hereby incorporated by reference. This article describes extracting the center line of a blood vessel.

The image analysis unit 610 may also perform image pre-processing in order to more accurately extract the center-line of the blood vessel from the medical image and acquire the first information as described in detail below. In detail, the image analysis unit 610 may remove at least one of a calcium area, a plaque area, and blood vessel branch points contained in the received medical image.

The operation of acquiring a first image and first information from the first image will now be described in more detail with reference to FIGS. 8 through 10.

In detail, the first image may be a longitudinal cross-section image of a blood vessel containing a center-line of the blood vessel. For example, the cross-section image of the blood vessel may be a curved planar reformation (CPR) image as described in detail below with reference to FIG. 8.

The first image may be a CT projection image acquired by projection on a plane having a normal perpendicular to the center-line of the blood vessel. Specifically, the first image may be a CT projection image acquired by projecting a 3D CT image on a direction parallel to a vertical vector of the center-line of the blood vessel.

Furthermore, if a 3D CT image (hereinafter, referred to as a multi-energy CT image) acquired by multi-energy CT imaging after injecting contrast media is input as a medical image, the first image may be a portion of the multi-energy CT image showing a portion of a blood vessel, a projection image for the multi-energy CT image, or a portion of the multi-energy CT image showing a cross-section of the blood vessel. The multi-energy CT image will be described in detail below with reference to FIG. 9.

Furthermore, the first information corresponds to an intensity value of an image signal from each of the normal and stenosis blood vessel region in the first image. For example, an intensity value of an image signal may be a magnitude of the image signal corresponding to each pixel, a brightness value of each pixel in an image, or a voltage that is applied to each pixel to generate an image.

The measuring unit 630 acquires first information corresponding to brightness intensities of normal and stenosis regions of a blood vessel from a first image and generates second information indicating the degree of stenosis of the blood vessel by using the first information. The operation of generating the second information from the first information will now be described in detail with reference to FIGS. 8 through 10.

Figure 8A:
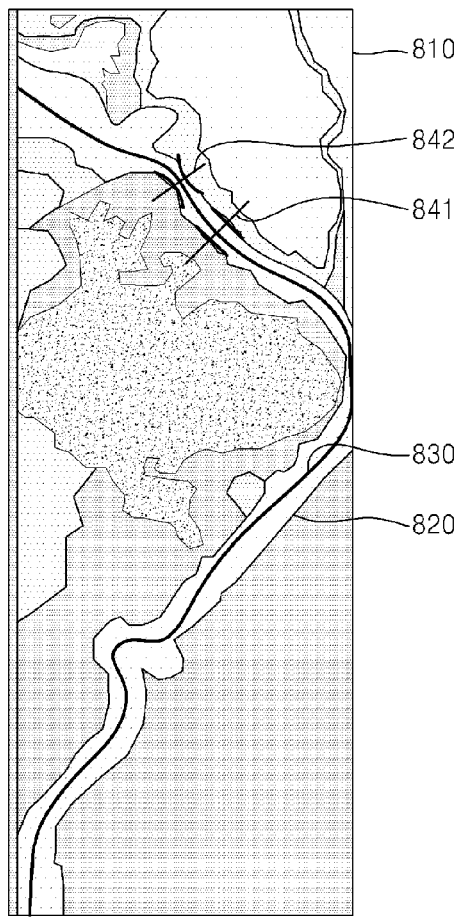
FIGS. 8A and 8B are diagrams for explaining the operation of an image analysis unit.
Figure 8B:
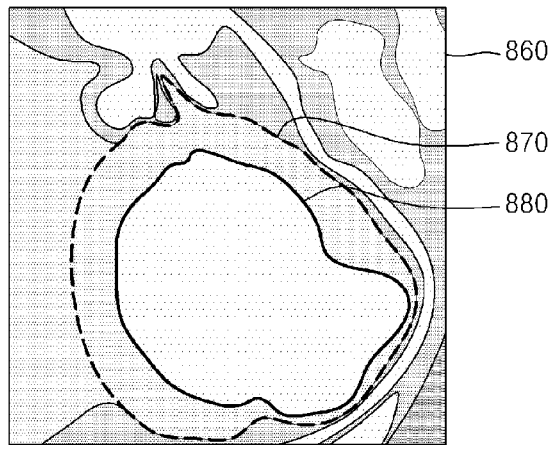

FIGS. 8A and 8B are diagrams for explaining the operation of the image analysis unit 610 in the apparatus 600 of FIG. 6.

FIG. 8A illustrates a cross-sectional CT image 810. In detail, the cross-sectional CT image 810 is obtained by imaging a coronary artery of the heart. FIG. 8B illustrates a cross-section image 860 of a blood vessel perpendicular to a center-line 830 of the blood vessel 820. The cross-section CT image 810 shows a cross-section taken along a center-line of the blood vessel in a first image corresponding to regions of blood vessels.

The image analysis unit 610 may acquire normal and stenosis regions of a blood vessel from the first image.

In detail, positions of the normal and stenosis blood vessels may be designated by a user and input from the user through the I/O unit 650. Alternatively, the image analysis unit 610 may automatically extract the positions of the normal and stenosis blood vessels.

For example, the I/O unit 650 may include the input unit 128 and the display unit 129 described with reference to FIG. 2. The I/O unit 650 may display the first image and receive normal and stenosis regions of the blood vessel in the first image from the user. The image analysis unit 610 may then receive the normal and stenosis regions of the blood vessel input through the I/O unit 650.

Alternatively, the image analysis unit 610 may track a diameter of a blood vessel in the first image and automatically extract normal blood vessel region and the stenosis blood vessel region based on a change in the diameter of the blood vessel.

In detail, when stenosis of the blood vessel occurs, a diameter of the blood vessel decreases and then increases again at a portion of the blood vessel where stenosis occurs as indicated by reference numeral 842. Thus, the image analysis unit 610 may track a diameter of the blood vessel to extract at least one region where stenosis occurs. In detail, the image analysis unit 610 may track a diameter of the blood vessel to extract a region where the diameter of the blood vessel remains unchanged as a normal blood vessel region. On the other hand, if the diameter of the blood vessel decreases to more than a predetermined value and then increases again in a certain area, the image analysis unit 610 may extract a position of the blood vessel having the smallest diameter as a stenosis blood vessel region.

Referring to FIG. 8A, a user may interpret the cross-sectional CT image 810 displayed on the I/O unit 650 and designate positions of normal and stenosis regions 841 and 842 of the blood vessel through the I/O unit 650. Then, the image analysis unit 610 may receive information about the designated positions from the I/O unit 650.

Furthermore, the image analysis unit 610 may output a user interface screen on which automatically extracted points are indicated in the cross-section CT image 810, thereby allowing the user to easily identify points where stenosis occurs and select at least one of the extracted points as a position of the stenosis blood vessel region.

FIG. 8B illustrates the cross-section image 860 of a stenosis region 880 of the blood vessel perpendicular to the center-line 830 of the blood vessel.

As apparent from FIG. 8B, the cross-section image 860 shows a distorted shape of the stenosis region 880. The stenosis region 880 of the blood vessel has a smaller diameter and a smaller area than a normal region 870 thereof.

As illustrated FIGS. 8A and 8B, in a CT image or a CT projection image, the blood vessel appears bright while tissues adjacent to the blood vessel appear dark.

Figure 9:
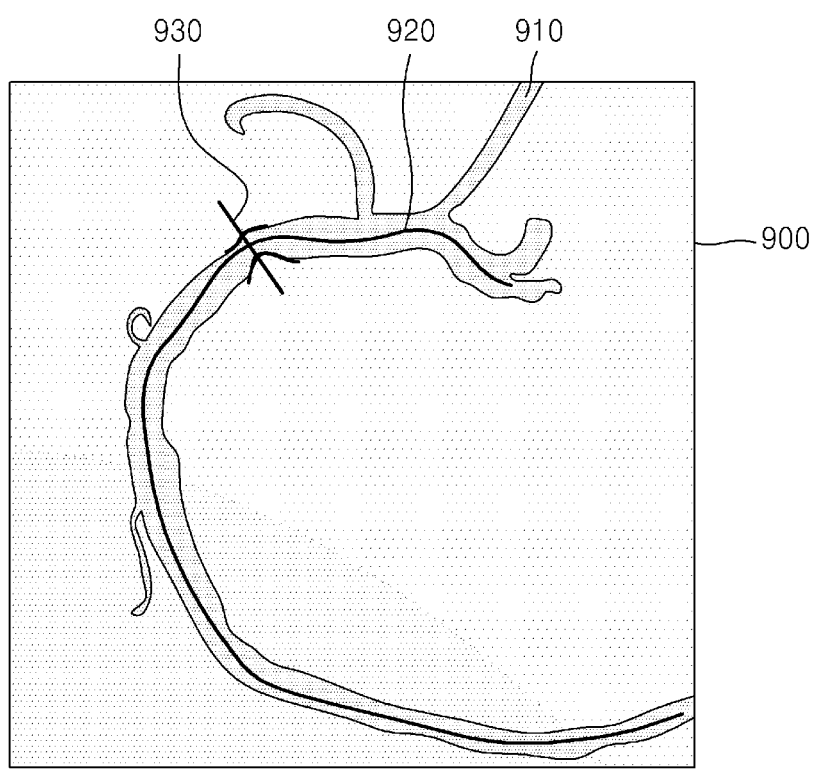
FIG. 9 is another diagram for explaining the operation of an image analysis unit.

FIG. 9 is another diagram for explaining the operation of the image analysis unit 610.

In particular, FIG. 9 illustrates a multi-energy CT image 900 acquired using multi-energy CT imaging after injecting contrast media into the body. When the contrast media is injected into the body for the multi-energy CT imaging, a portion of a blood vessel 910 may become clearly visible in an image. That is, a CT image obtained by the multi-energy CT imaging after injecting the contrast media may clearly represent a position, a shape, and a dimension of a blood vessel in a part of a body being imaged. The CT image obtained after injection of the contrast media may be hereinafter referred to as a blood vessel map or iodine map.

Referring to FIG. 9, the multi-energy CT image 900 obtained by using the contrast media exhibits a boundary of a blood vessel more clearly than a general CT image obtained without the contrast media. Thus, the image analysis unit 610 may accurately acquire positions of normal and stenosis regions of the blood vessel by using the multi-energy CT image 900.

Furthermore, an image of a cross-section of a region 930 where stenosis occurs and taken along a center-line 920 of the blood vessel may be used for a subsequent process of acquiring first information.

Figure 10A:
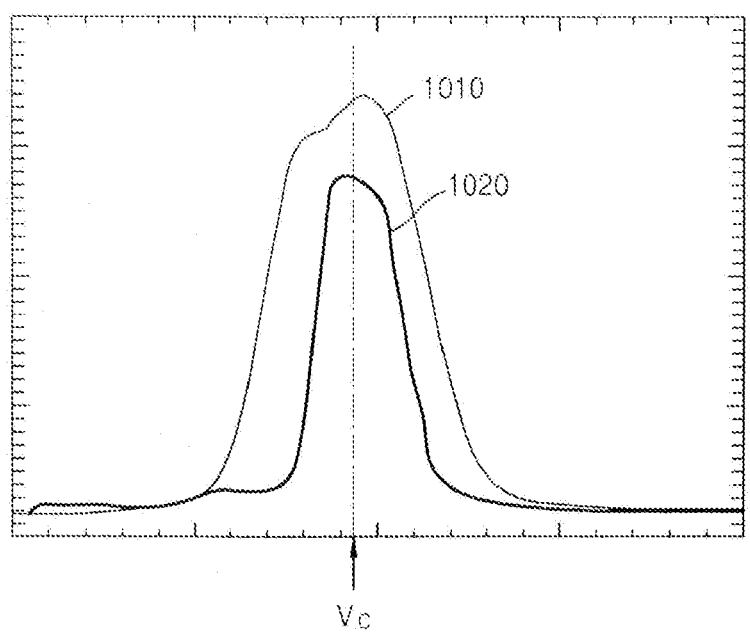
FIGS. 10A and 10B are diagrams for explaining an operation of a measuring unit.
Figure 10B:
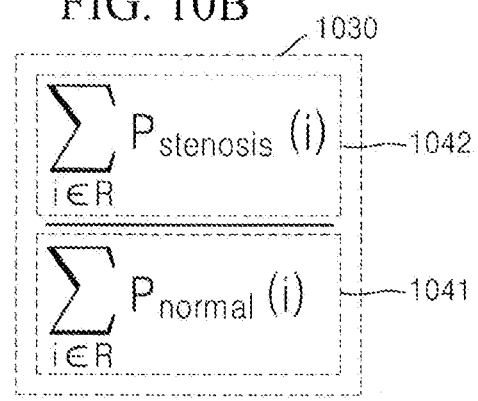

FIGS. 10A and 10B are diagrams for explaining an operation of the measuring unit 630 in the apparatus 600 of FIG. 6.

The measuring unit 630 measures the degree of stenosis of a blood vessel by using intensity values of an image signal in the first image. As described above, intensity values of image signals from a blood vessel region and a non-blood vessel region are different from each other. That is, the blood vessel region appears bright while adjacent tissues to the blood vessel appear dark. Thus, based on this principle, the apparatus 600 is configured to measure the degree of stenosis of a blood vessel by using intensity values of image signals in an image.

In detail, the measuring unit 630 acquires first information corresponding to brightness intensities from the first image.

Referring back to FIG. 8, in the cross-sectional CT image 810, the first information corresponds to image brightness values of the normal and stenosis regions 841 and 842 of the blood vessel perpendicular to the center-line 830 thereof. Although the normal and stenosis regions 841 and 842 are indicated by lines in FIG. 8, respectively, they may be sections having predetermined sizes. The length of the lines and the number of image brightness value, e.g. pixel or voxel values, may be predetermined, i.e. the same for the normal region and the stenosis region.

The first information includes for each of the normal region and stenosis region a value corresponding to a linear combination of the brightness values of the respective region. The linear combination includes a linear combination of at least two brightness values. The values are calculated by measuring unit 630. In detail, the first information may include a first cumulative value corresponding to a stenosis blood vessel region and a second cumulative value corresponding to a normal region thereof.

The first cumulative value is obtained by accumulating image brightness values of a first portion of the stenosis blood vessel region perpendicular to the center-line 830 thereof in the first image.

The second cumulative value is obtained by accumulating image brightness values of a second portion of the normal blood vessel region perpendicular to the center-line 830 thereof in the first image.

The measuring unit 630 may acquire second information by using the first and second cumulative values. For example, the measuring unit 630 calculates the ratio or difference between the first and second cumulative values to quantify the degree of stenosis of the body lumen in the stenosis body lumen region. FIG. 10 illustrates an example in which the measuring unit 630 calculates the first and second cumulative values by using the cross-sectional CT image 810 illustrated in FIG. 8. Furthermore, the measuring unit 630 may acquire the first information by using all medical images that represent a blood vessel and tissue other than the blood vessel via different brightness intensities, i.e., intensity values of image signals, such as the segmented image 700, the cross-sectional CT image 810, a CT projection image, or the multi-energy CT image 900 obtained by multi-energy CT imaging after contrast media are injected. In addition to the first and second cumulative values, all values that can represent intensities of image signals may be used as the first information. Brightness intensity graphs 1010 and 1020 illustrated in FIG. 10 may also be used as the first information.

An operation of acquiring second information in the measuring unit 630 will now be described in more detail with reference to FIG. 10.

FIG. 10 illustrates the brightness intensity graphs 1010 and 1020 showing brightness intensities of the normal and stenosis regions 841 and 842 of the blood vessel illustrated in FIG. 8, respectively. In the brightness intensity graphs 1010 and 1020, the abscissa represents a position along the normal and stenosis regions 841 and 842 and the lines in FIG. 8 indicating the normal and stenosis regions 841 and 842. The ordinate denotes an intensity value of image signals, i.e., a brightness intensity, at the normal and stenosis regions 841 and 842 indicated by the lines.

As described above, a CT image, a cross-section image of a blood vessel, a CT projection image, or a multi-energy CT image obtained after injection of contrast media shows an area within the blood vessel as a bright area and tissue outside the blood vessel as a dark area. In other words, in the first image, intensity values of image signals in a blood vessel region increase while those of image signals in a non-blood vessel region decrease.

Of course, the images may alternatively be displayed as negative images, in that case the bright area will be within the blood vessel and the dark area will be the tissue outside the blood vessel.

Referring to FIG. 10, each of the brightness intensity graphs 1010 and 1020 has a maximum brightness intensity at a center Vc of the blood vessel passing through the center-line thereof.

In Equation 1030 illustrated in FIG. 10, Pnormal and Pstenosis denote functions respectively corresponding to the brightness intensity graphs 1010 and 1020 representing brightness intensities of the normal and stenosis regions 841 and 842 of the blood vessel. R and i denote a predetermined area including a blood vessel and an intensity value of an image signal included in the predetermined area R, respectively. The predetermined area R may include all points on a line corresponding to the position of the normal or stenosis regions 841 or 842 of the blood vessel as illustrated in FIG. 8, or include the normal and stenosis regions 841 and 842 of the blood vessel.

In detail, in Equation 1030, a reference numeral 1041 denotes a second cumulative value acquired by accumulating or summing brightness values of the normal region 841 of the blood vessel perpendicular to the central-line 830 thereof, and a reference numeral 1042 denotes a first cumulative value acquired by accumulating or summing brightness values of the stenosis region 842 of the blood vessel perpendicular to the central-line 830 thereof.

In other words, the first cumulative value may be obtained by integrating intensity values of image signals over the predetermined area (e.g., 842) including the stenosis region of the blood vessel. Similarly, the second cumulative value may be obtained by integrating intensity values of image signals over the predetermined area (e.g., 841) including the normal region of the blood vessel.

The measuring unit 630 may acquire second information by using the first and second cumulative values. In detail, as defined by Equation 1030 in FIG. 10, the measuring unit 630 may generate the second information based on a ratio between the first and second cumulative values. Alternatively, the measuring unit 630 may generate the second information by using a difference between the first and second cumulative values.

In addition to the ratio or difference between the first and second cumulative values, the measuring unit 630 may generate the second information by using all types of information that can be used to compare or contrast signal intensity values of a normal blood vessel region with those of a stenosis blood vessel region.

The second information calculated by the measuring unit 630 may be output through the I/O unit 650 so that the user can recognize it. The user may then detect the degree of stenosis of a blood vessel based on the second information.

The above example described acquiring the intensities of a normal region and stenosis region on the basis of an image wherein the center line of the blood vessel is visible, i.e. the longitudinal extension of the center line is visible. However, according to the invention, intensities may alternatively be obtained of images of the cross section of the blood vessel, as shown in FIG. 8B. In such an embodiment, two cross sections are obtained from 3D medical image data. The first cross section corresponds to the normal blood vessel region and the second cross section corresponds to the stenosis blood vessel region. The cross sections are taken along a plane perpendicular to the center line of the blood vessel. FIG. 8B shows the cross section for the stenosis blood vessel region. In this embodiment, the second information may be obtained by obtaining the sum or weighted sum of the intensities, i.e. pixel values, of the cross section image. The sum or weighted sum of the pixels of the cross section image of the stenosis blood vessel region (FIG. 8B) will in general be less than the sum of the pixels of the cross section image of the normal blood vessel region. The second information may include the ratio or difference between the calculated sum or weighted sum of the two regions FIG. 11 is a block diagram of an apparatus 1100 for processing a medical image according to another exemplary embodiment of the present invention.

Figure 11:
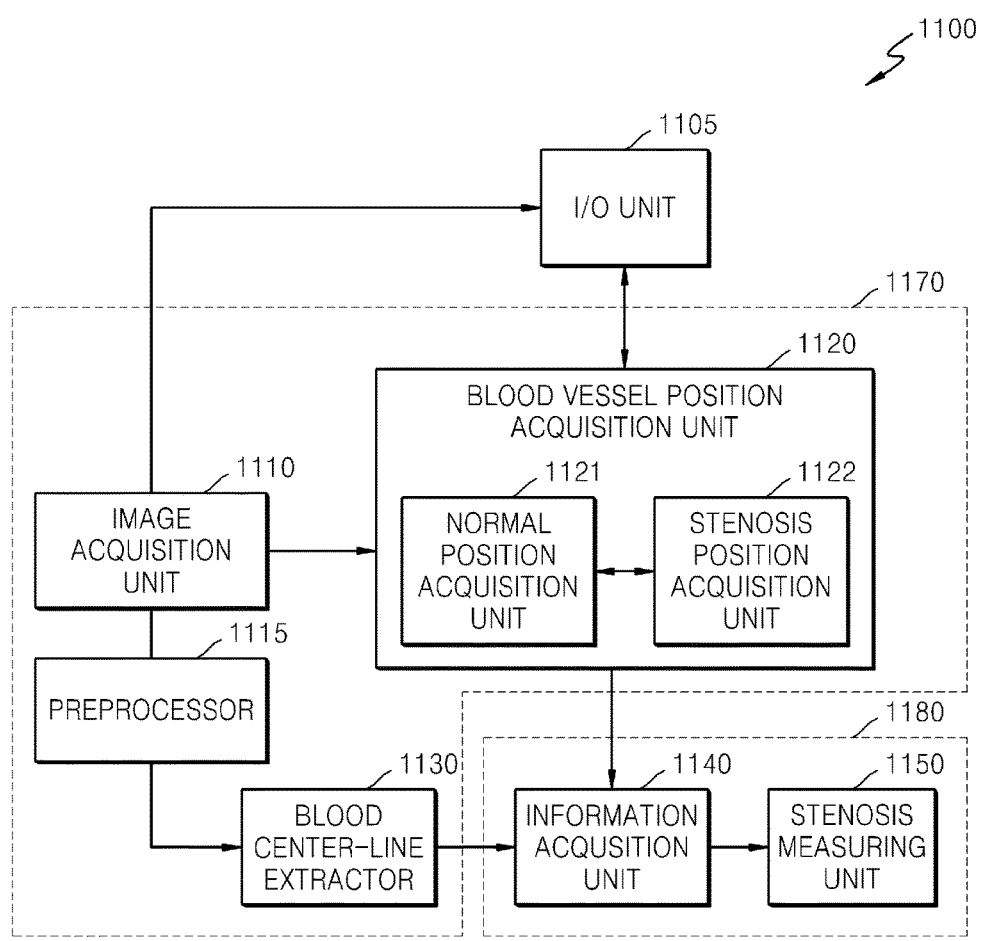
FIG. 11 is a block diagram of an apparatus for processing a medical image according to another exemplary embodiment of the present invention.

Referring to FIG. 11, the apparatus 1100 according to the present embodiment includes an image analysis unit 1170, a measuring unit 1180, and an I/O unit 1105. The image analysis unit 1170, the measuring unit 1180, and the I/O unit 1105 in the apparatus 1100 may have substantially the same configurations and functions as those of their counterparts in the apparatus 600 in FIG. 6. Thus, the same descriptions as presented with respect to FIG. 6 are not repeated.

Referring to FIG. 11, the image analysis unit 1170 includes an image acquisition unit 1110, a preprocessor 1115, a blood vessel position acquisition unit 1120, and a blood vessel center-line extractor 1130. The measuring unit 1180 includes an information acquisition unit 1140 and a stenosis measuring unit 1150. The blood vessel position acquisition unit 1120 may include a normal position acquisition unit 1121 and a stenosis position acquisition unit 1122.

The image acquisition unit 1110 receives a medical image as an input. In detail, the image acquisition unit 1110 may reconstruct a 3D CT image by using an electrical signal acquired by the DAS (116 in FIG. 2), or receive a reconstructed CT image from the outside. The image acquisition unit 1110 also acquires a first image corresponding to a portion of a blood vessel from the medical image.

The preprocessor 1110 performs image pre-processing on a medical image acquired by the image acquisition unit 1110. Specifically, the preprocessor 1110 may remove at least one of a calcium area, a plaque area, and blood vessel branch points contained in the medical or the first image.

The blood vessel position acquisition unit 1120 acquires normal and stenosis regions of a blood vessel from the first image.

In detail, the normal position acquisition unit 1121 and the stenosis position acquisition unit 1122 acquire normal and stenosis regions of the blood vessel from the first image, respectively.

The blood vessel position acquisition unit 1120 segments a portion of the blood vessel in a CT image and acquires a first image and normal and stenosis regions of the blood vessel from the first image. The blood vessel position acquisition unit 1120 may also acquire the normal and stenosis regions of the blood vessel from a CT projection image or a cross-section image of a blood vessel center-line.

As described above, the normal and stenosis regions of the blood vessel may be automatically acquired or manually acquired according to a user input.

The blood vessel center-line extractor 1130 extracts a center-line of the blood vessel from the medical image.

The information acquisition unit 1140 acquires first information corresponding to brightness intensities of images in each of the normal and stenosis regions of the blood vessel in the first image and perpendicular to the center-line of the blood vessel. More specifically, the first information may include the first and second cumulative values described above.

The measuring unit 1150 generates second information indicating the degree of stenosis of a blood vessel based on the first information acquired by the information acquisition unit 1140.

Figure 12:
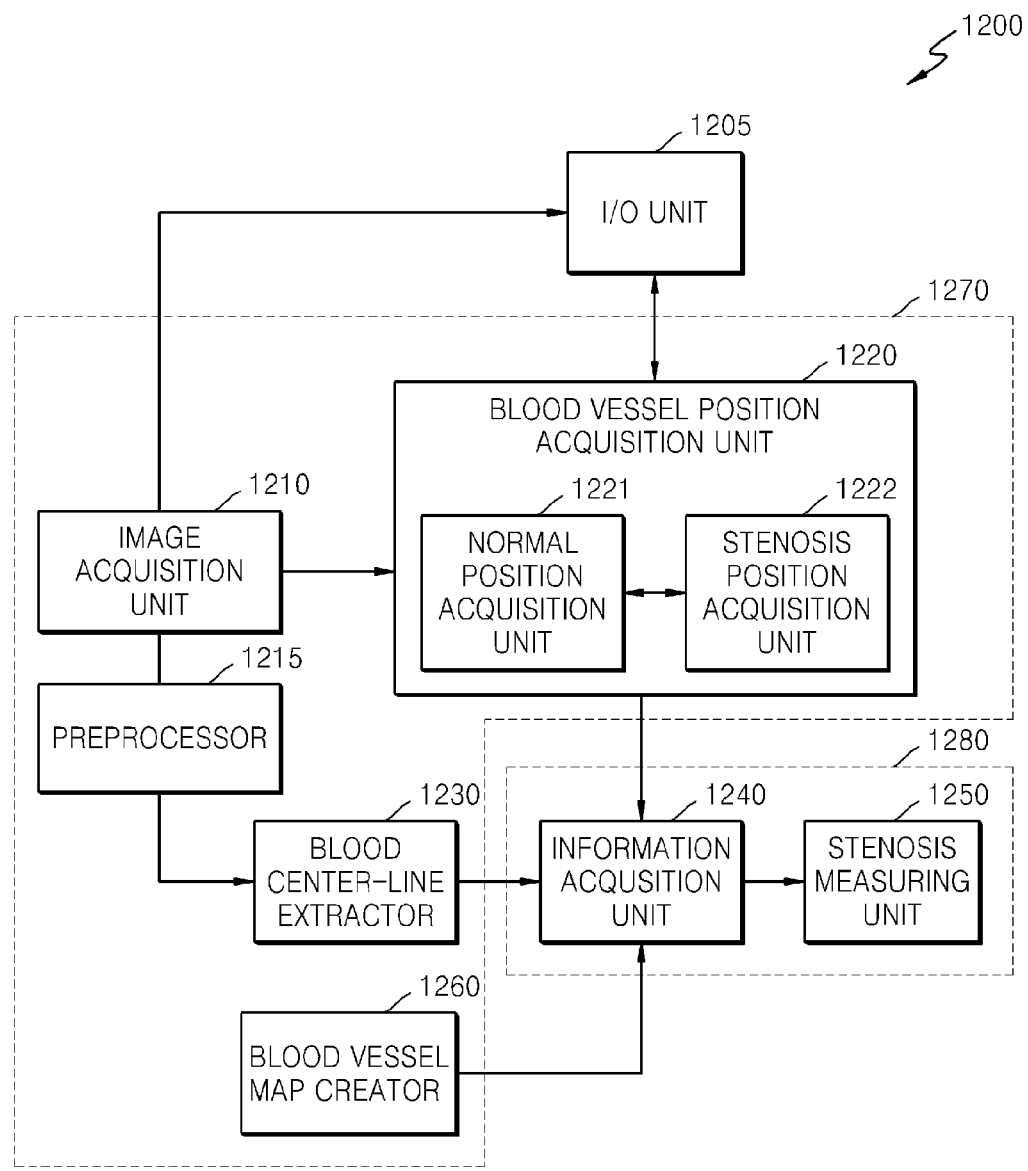
FIG. 12 is a block diagram of an apparatus for processing a medical image according to another exemplary embodiment of the present invention.

FIG. 12 is a block diagram of an apparatus 1200 for processing a medical image according to another exemplary embodiment of the present invention.

In the apparatus 1200 according to the present embodiment, an I/O unit 1205, an image analysis unit 1270, a normal position acquisition unit 1221, a stenosis position acquisition unit 1222, a measuring unit 1280, an image acquisition unit 1210, a preprocessor 1215, a blood vessel position acquisition unit 1220, a blood vessel center-line extractor 1230, an information acquisition unit 1240, and a measuring unit 1250 may have substantially the same configurations and functions as their counterparts in the apparatus 1100 in FIG. 11. Thus, the same descriptions as already described with respect to FIGS. 6 and 11 are not repeated.

Referring to FIG. 12, the apparatus 1200 is different from the apparatus 1100 in that it may further include a blood vessel map creator 1260.

The blood vessel map creator 1260 may receive a blood vessel map from the outside or create a blood vessel map by using a medical image acquired by the image acquisition unit 1210. In detail, the blood vessel map creator 1260 may generate a CT image by using multi-energy CT imaging after injection of contrast media The apparatus 1200 is also different from the apparatus 1100 of FIG. 11 in that it generates first information by using a multi-energy CT image. The rest of the structure and operation is the same as those of the apparatus 1110.

Figure 13:
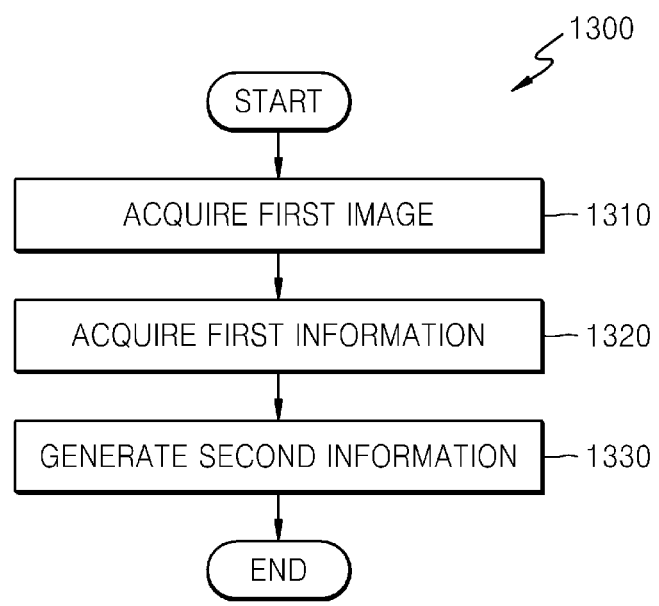
FIG. 13 is a flowchart of a method of processing a medical image according to an exemplary embodiment of the present invention.

FIG. 13 is a flowchart of a method 1300 of processing a medical image according to an exemplary embodiment of the present invention.

The method 1300 according to the present embodiment has the same technical idea as the apparatuses 600, 1100, and 1200 for processing a medical image according to the embodiments of the present invention. Thus, the same descriptions as already described with respect to FIGS. 1 through 12 are not repeated. The method 1300 will now be described with reference to FIGS. 6 and 13.

Referring to FIG. 13, a first image corresponding to a portion of a blood vessel is acquired from a medical image obtained by emitting radiation (operation 1310). The operation 1310 may be performed by the image analysis unit 610. The medical image may be a 3D CT image. The medical image may also be a multi-energy CT image obtained by multi-energy CT imaging after injection of contrast media.

First information corresponding to brightness intensities of normal and stenosis regions of the blood vessel is acquired from the first image (operation 1320). The operation 1320 may be performed by the measuring unit 630. In the operation 1320, the brightness intensities may be intensity values of image signals in an image.

In detail, a first cumulative value may be acquired by accumulating image brightness values in the first image. A second cumulative value may also be acquired by accumulating brightness values of a normal region of a blood vessel in the first image.

Second information indicating the degree of stenosis of the blood vessel is generated by using the first information acquired in the operation 1320 (operation 1330). The operation 1330 may be performed by the measuring unit 630. For example, the second information may be generated by using a ratio between the first and second cumulative values.

Figure 14:
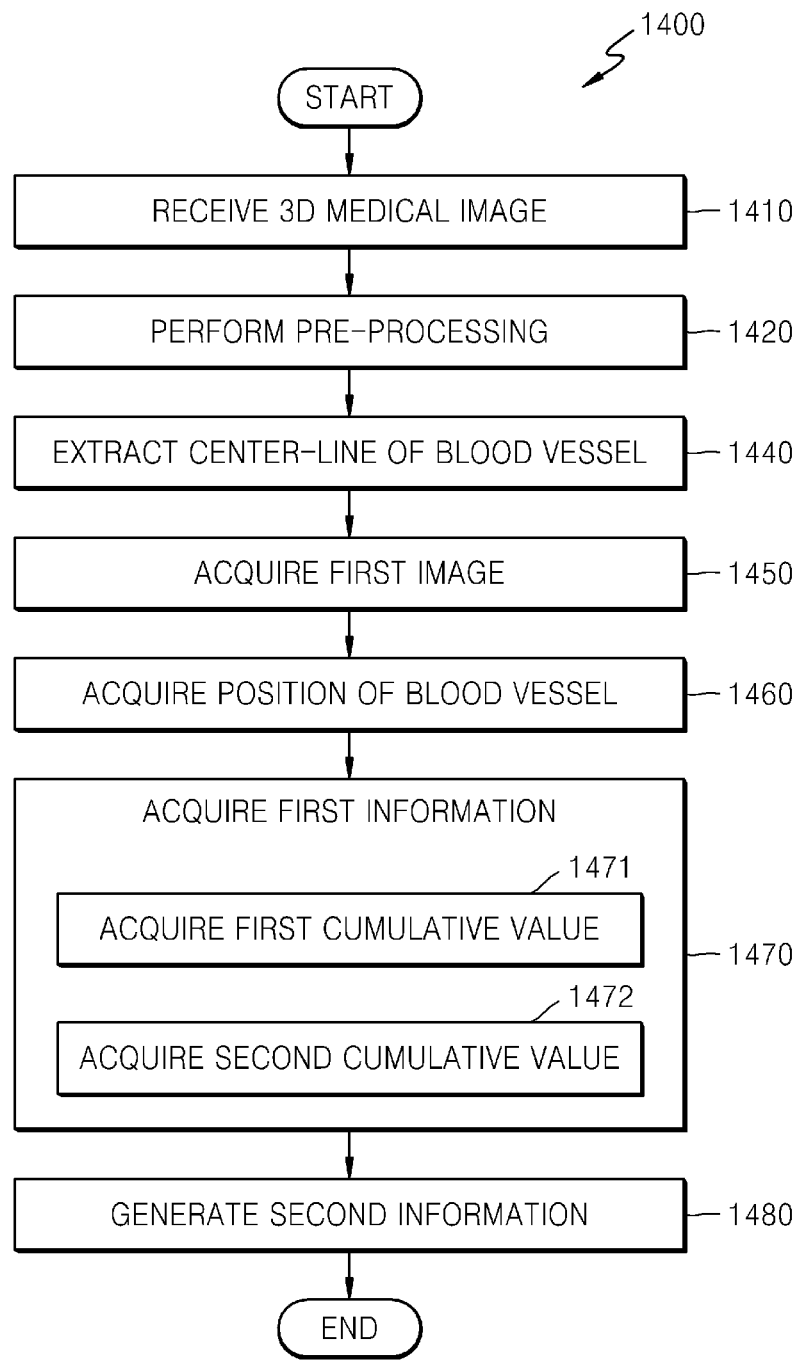
FIG. 14 is a flowchart of a method of processing a medical image according to another exemplary embodiment of the present invention.

FIG. 14 is a flowchart of a method 1400 of processing a medical image according to another exemplary embodiment of the present invention.

The method 1400 according to the present embodiment has the same technical idea as the apparatuses 600, 1100, and 1200 for processing a medical image according to the embodiments of the present invention. Thus, the same descriptions as already presented with respect to FIGS. 1 through 12 are not repeated. The method 1400 will now be described with reference to FIGS. 6 and 14.

A 3D medical image is received (operation 1410). The operation 1410 may be performed by the image analysis unit 610.

Image pre-processing is performed on the received 3D medical image (operation 1420). The operation 1420 may be performed by the image analysis unit 610.

A center-line of a blood vessel is extracted from a portion of the blood vessel in the received medical image (operation 1440). The operation 1440 may be performed by the image analysis unit 610.

A first image corresponding to the portion of the blood vessel is acquired from the pre-processed 3D medical image (operation 1450). Operation 1450 may be performed by the image analysis unit 610. In this case, the first image may be an image clearly showing a blood vessel where stenosis occurs and the degree of stenosis of which is to be measured. In detail, a CT projection image may be acquired as the first image by projecting a medical image of a portion of a blood vessel on a direction perpendicular to the center-line of the blood vessel. Alternatively, a cross-section image containing the center-line of the blood vessel may be acquired as the first image by cutting along the center-line thereof in a medical image corresponding to the portion of the blood vessel.

Normal and stenosis regions of the blood vessel are acquired from the 3D medical image (operation 1460). The operation 1460 may be performed by the image analysis unit 610. As described above, the normal and stenosis regions of the blood vessel may be acquired automatically by the image analysis unit 610 or manually according to user's designation.

First information corresponding to brightness intensities of images at each of the normal and stenosis regions of the blood vessel is acquired (operation 1470). The operation 1470 may be performed by the measuring unit 630. In detail, the first information may be information corresponding to intensity values of image signals from each of the normal and stenosis regions of the blood vessel.

In detail, a first cumulative value is acquired by accumulating image brightness values of a portion of the stenosis blood vessel region perpendicular to the center-line of the blood vessel in the first image (operation 1471). A second cumulative value is also acquired by accumulating image brightness values of a portion of the normal blood vessel region perpendicular to the central-line thereof in the first image (operation 1472).

Second information indicating the degree of stenosis of the blood vessel is generated by using the first information acquired in the operation 1470 (operation 1480). The operation 1480 may be performed by the measuring unit 630.

In detail, the second information may be generated by using a ratio between the second and first cumulative values or a difference therebetween.

Although not shown in FIG. 14, the method 1400 may further include displaying the second information to a user. The operation may be performed by the I/O unit 650. Furthermore, the second information and the first image may be displayed together on the same screen.

As described above, an apparatus and method for processing a medical image according to one or more embodiments of the present invention are adapted to accurately measure the degree of stenosis of a blood vessel by using brightness intensities of a cross-section image perpendicular to a center-line of the blood vessel.

In a related art method of measuring the degree of stenosis of a blood vessel, the accuracy of measuring the diameters of normal and stenosis blood vessels is low due to a lower resolution of a CT image. In detail, although an intensity value of an image signal in a CT image corresponds to 0.7 mm, a coronary artery has a diameter of about 2 to 3 mm. Thus, it may be difficult to accurately segment a stenosis region of a blood vessel and measure a diameter of the blood vessel.

On the other hand, an apparatus and method for processing a medical image according to one or more embodiments of the present invention may be used to measure the degree of stenosis of a blood vessel based on brightness intensities of a cross-section image perpendicular to a center-line of the blood vessel, thereby allowing an accurate measurement of the degree of stenosis of the blood vessel in a CT image. In detail, a value obtained by accumulating or summing brightness values of a cross-section image of a blood vessel is affected little by a resolution of a CT image. Thus, if the degree of stenosis of the blood vessel is measured based on a sum of brightness values of a region of a blood vessel within a cross-section image, it is possible to accurately measure the degree of stenosis of the blood vessel even in a low-resolution CT image.

In the above embodiments, the measuring unit is configured to quantify the degree of stenosis of the body lumen in a stenosis region. Additionally or alternatively, the apparatus may track the value of the linear combination for different regions along the center line, and a stenosis region may be detected based on a change in the calculated value.

In detail, when stenosis of the blood vessel occurs, the value of a linear combination of brightness intensities in the region of stenosis will differ from the value in normal regions, i.e. regions without stenosis. The image analysis unit 610 or measuring unit 630 may calculate the value of the linear combination for different regions of the blood vessel to extract at least one region where stenosis occurs. In detail, the apparatus may determine regions where the calculated value remains substantially the same as normal blood vessel regions. On the other hand, if the calculated value of a region differs from the value of adjacent regions by a predetermined fraction, the apparatus may extract said region as a stenosis blood vessel region. In other words, the comparison between the first body lumen value and the second body lumen value may be used to detect a stenosis region and a normal region. Subsequently, the degree of stenosis of the detected stenosis region may be quantified on the basis of the calculated value for the stenosis region and the normal region.

The above embodiments of the present invention can be recorded in programs that can be executed on a computer and be implemented through general purpose digital computers which can run the programs using a computer-readable recording medium.

Examples of the computer-readable recording medium include recording media, such as magnetic storage media (e.g., ROM, floppy disks, hard disks, etc.), optical recording media (e.g., CD-ROMs or DVDs), and carrier waves (e.g., transmission through the Internet).

While one or more embodiments of the present invention have been described with reference to the figures, it will be understood by those of ordinary skill in the art that various changes in form and details may be made therein without departing from the spirit and scope of the present invention as defined by the following claims. Thus, it should be understood that the exemplary embodiments described therein should be considered in a descriptive sense only and not for purposes of limitation.

The invention claimed is:

1. An apparatus for processing a medical image of a body lumen, the apparatus comprising:
    an image processor configured to:
        extract, from the medical image, brightness intensities corresponding to pixel values in a normal body lumen region of the medical image, the normal body lumen region being an image area on a first cross section substantially perpendicular to a center line of the body lumen,
        extract brightness intensities corresponding to pixel values in a stenosis body lumen region of the medical image, the stenosis body lumen region being an image area on a second cross section which is different from the first cross section and substantially perpendicular to the center line of the body lumen,
        calculate a first sum of the brightness intensities of the pixel values of the image area of the first cross section,
        calculate a second sum of the brightness intensities of the pixel values of the image area of the second cross section, and
        generate a measure of a degree of stenosis of the body lumen as a ratio, by dividing the second sum by the first sum, or as a difference between the first sum and the second sum, without calculating a size of an area of the stenosis body lumen region.

2. The apparatus of claim 1, wherein the image processor is further configured to extract the center line of the body lumen from the medical image,
    the normal body lumen region is substantially perpendicular to the center line of the body lumen at a first position along the center line, and
    the stenosis body lumen region is substantially perpendicular to the center line at a second position along the center line, different from the first position.

3. The apparatus of claim 2, wherein the medical image is a three-dimensional (3D) medical image, and the image processor is further configured to extract, from the 3D medical image, a projection image by projecting the medical image on a plane having a normal substantially perpendicular to the center line of the body lumen, and to extract the brightness intensities of the normal body lumen region and the stenosis body lumen region from the projection image.

4. The apparatus of claim 2, wherein the medical image is a two-dimensional (2D) medical image corresponding to a projection image of the body lumen in a plane having a normal substantially perpendicular to the center line of the body lumen, and
the image processor is further configured to extract the brightness intensities of the normal body lumen region and the stenosis body lumen region from the projection image.

5. The apparatus of claim 2, wherein the medical image is a three-dimensional (3D) medical image, and
the image processor is further configured to extract, from the 3D medical image, an image of the first cross section of the body lumen in a plane substantially perpendicular to the center line at the first position and an image of the second cross section of the body lumen in a plane substantially perpendicular to the center line at the second position, and to extract the brightness intensities of the normal body lumen region from the image of said first cross section and extract the brightness intensities of the stenosis body lumen region from the image of said second cross section.

6. The apparatus of claim 1, further comprising a user input unit configured to receive an input of the normal body lumen region and the stenosis body lumen region from a user.

7. The apparatus of claim 1, wherein the image processor is further configured to identify a diameter of the body lumen based on the medical image and to extract the normal body lumen region and the stenosis body lumen region based on a change in the diameter of the body lumen.

8. The apparatus of claim 1, wherein the medical image is a computed tomography (CT) image obtained by a multi-energy CT image capturing after injection of contrast media.

9. The apparatus of claim 1, wherein the body lumen is a blood vessel.

10. A method of processing a medical image of a body lumen by using a medical image apparatus, the method comprising:
performing, by an image processor of the medical image apparatus, operations of:
extracting, from the medical image, brightness intensities corresponding to pixel values in a normal body lumen region of the medical image, the normal body lumen region being an image area on a first cross section substantially perpendicular to a center line of the body lumen;
extracting, from the medical image, brightness intensities corresponding to pixel values in a stenosis body lumen region of the medical image, the stenosis body lumen region being an image area on a second cross section which is different from the first cross section and substantially perpendicular to the center line of the body lumen;
calculating a first sum of the brightness intensities of the pixel values of the image area of the first cross section;
calculating a second sum of the brightness intensities of the pixel values of the image area of the second cross section; and
generating a measure of a degree of stenosis of the body lumen as a ratio of the second sum to the first sum or as a difference between the first sum and the second sum, the ratio is being calculated by dividing the second sum by the first sum, the ratio is being calculated by dividing the second sum by the first sum, without calculating a size of an area of the stenosis body region.

11. The method of claim 10, further comprising:
performing, by the image processor, an operation of extracting the center line of the body lumen from an area of the body lumen,
wherein the normal body lumen region is substantially perpendicular to the center line of the body lumen at a first position along the center line, and
the stenosis body lumen region is substantially perpendicular to the center line at a second position along the center line, different from the first position.

12. The method of claim 11, wherein the medical image is a three-dimensional (3D) medical image, and the method further comprises:
performing, by the image processor, operations of:
extracting, from the 3D medical image a projection image by projecting the medical image on a plane having a normal substantially perpendicular to the center line of the body lumen; and
extracting, the brightness intensities of the normal body lumen region and the stenosis body lumen region from the projection image.

13. The method of claim 11, wherein the medical image is a two-dimensional (2D) medical image corresponding to a projection image of the body lumen in a plane having a normal substantially perpendicular to the center line of the body lumen, and
the method further comprises performing, by the image processor, an operation of extracting the brightness intensities of the normal body lumen region and the stenosis body lumen region from the projection image.

14. The method of claim 11, wherein the medical image is a three-dimensional (3D) medical image, and the method further comprises:
performing, by the image processor, operations of:
extracting, from the 3D medical image, an image of the first cross section of the body lumen in a plane substantially perpendicular to the center line at the first position;
extracting, an image of the second cross section of the body lumen in a plane substantially perpendicular to the center line at the second position; and
extracting, the brightness intensities of the pixel values in the normal body lumen region from the image of said first cross section and extracting the brightness intensities of the stenosis body lumen region from the image of said second cross section.

15. An apparatus for processing a medical image, the apparatus comprising:
an image processor configured to:
receive a medical image captured by emitting radiation,
acquire a first image corresponding to an area of a blood vessel, from the medical image,
acquire a normal blood vessel region and a stenosis blood vessel region from the first image,
extract a center line of the blood vessel from the area of the blood vessel,
acquire first information corresponding to brightness intensities of pixels in an image of regions corresponding to each of the normal blood vessel region and the stenosis blood vessel region, respectively, the normal blood vessel region and the stenosis blood vessel region being different regions perpendicular to the center line of the blood vessel, calculate a first sum of the brightness intensities of the pixels of the normal blood vessel region, calculate a second sum of the brightness intensities of the pixels of the stenosis blood vessel region, and generate a measure of a degree of stenosis of the blood vessel as a ratio, by dividing the second sum by the first sum, or as a difference between the first sum and the second sum, without calculating a size of an area of the stenosis body lumen region.

\* \* \* \* \*